United States Patent
Garcia et al.

(10) Patent No.: US 9,029,319 B1
(45) Date of Patent: May 12, 2015

(54) WATER BUFFALO DERIVED PEPTIDE ANTIBIOTIC THERAPIES

(71) Applicants: Luis Tonatiuh Melgarejo Garcia, Manhattan, KS (US); Annika Linde, Manhattan, KS (US); Gerald Henry Lushington, Lawrence, KS (US)

(72) Inventors: Luis Tonatiuh Melgarejo Garcia, Manhattan, KS (US); Annika Linde, Manhattan, KS (US); Gerald Henry Lushington, Lawrence, KS (US)

(73) Assignee: Centaur, Inc., Olathe, KS (US)

( * ) Notice: Subject to any disclaimer, the term of this patent is extended or adjusted under 35 U.S.C. 154(b) by 0 days.

(21) Appl. No.: 14/483,083

(22) Filed: Sep. 10, 2014

Related U.S. Application Data (60) Provisional application No. 62/032,737, filed on Aug. 4, 2014.

(51) Int. Cl.
| | |
|---|---|
| *A01N 37/18* | (2006.01) |
| *A61K 38/04* | (2006.01) |
| *C07K 14/00* | (2006.01) |
| *A01N 43/38* | (2006.01) |
| *A01N 47/44* | (2006.01) |

(52) U.S. Cl.
CPC ............... *C07K 14/00* (2013.01); *A01N 43/38* (2013.01); *A01N 47/44* (2013.01)

(58) Field of Classification Search
None
See application file for complete search history.

(56) References Cited

PUBLICATIONS

Das et al. Cloning and characterization of novel cathelicidin cDNA sequence of Bubalus bubalis homologous to Bos taurus cathelicidin-4. DNA Sequence, Dec. 2006. vol. 17, No. 6, pp. 407-414.*
Okuda et al. Determination of the Antibacterial and Lipopolysaccharide-Neutralizing Regions of Guinea Pig Neutrophil Cathelicidin Peptide CAP11. Antimicrobial Agents and Chemotherapy. Aug. 2006, pp. 20602-2607.*
Lee et al. Salt-resistant homodimeric bactenecin, a cathelicidin-derived antimicrobial peptide. The FEBS Journal, 2008. vol. 275, pp. 3911-3920.*
Jonson et al. A critical view on conservative mutations. Protein Engineering, 2001. vol. 14, No. 6, pp. 397-402.*
Haney et al., "Solution NMR studies of amphibian antimicobial peptides: Linking structure to function?", Biochimica et Biophysica Acta, 1788 (2009) pp. 1639-1655.

* cited by examiner

*Primary Examiner* — Marcela M Cordero Garcia
(74) *Attorney, Agent, or Firm* — Polsinelli PC (57) ABSTRACT

The present disclosure relates to antimicrobial agents and methods of using such agents. The disclosure includes antimicrobial agents having broad spectrum antimicrobial activity, nucleic acids and amino acid sequences encoding such antimicrobial agents, as well as methods of using the antimicrobial agents. The antimicrobial agents of the disclosure may be used to reduce survival of a microbe, as an antimicrobial therapeutic, in microbial treatment protocols, and in research, as well as other uses related to reducing microbe survival. In addition, the disclosure also includes compositions, as well as articles of manufacture, that comprise a broad spectrum antimicrobial agent.

28 Claims, 5 Drawing Sheets

WATER BUFFALO DERIVED PEPTIDE ANTIBIOTIC THERAPIES

FIELD OF THE INVENTION

The present disclosure relates to antimicrobial agents and methods of using. More particularly, the disclosure relates to antimicrobial peptides and therapeutic uses thereof.

SEQUENCE LISTING

This application contains a sequence listing in paper format and in computer readable format, the teachings and content of which are hereby incorporated by reference.

BACKGROUND OF THE INVENTION

Antimicrobial resistance is reducing the availability of effective antimicrobial treatments worldwide. Resistant organisms, including bacteria, fungi, viruses, and parasites, are able to withstand attack by antimicrobial medicines, so that standard treatments become ineffective. Infections by such resistant organisms persist increasing the risk of spreading to others. The evolution of resistant strains of organisms is a natural phenomenon that occurs when microorganisms are exposed to antimicrobial drugs, and resistant traits can be exchanged between certain types of bacteria. The misuse of antimicrobial medicines also accelerates the emergence of resistant organisms.

With the decrease in effective antimicrobial treatments due to the emergence of resistant organisms, new antimicrobial therapeutics are needed. The number of new antimicrobial therapies developed and approved has steadily decreased in the past three decades, leaving even fewer options to treat resistant organisms.

Accordingly, a need exists for antimicrobial treatments and therapeutics having broad spectrum antimicrobial activity. Moreover, a need exists for effectively inhibiting the growth and spread of harmful microorganisms.

SUMMARY OF THE INVENTION

The present disclosure provides antimicrobial agents having broad spectrum antimicrobial activity and methods of inhibiting microorganism growth. In particular, the present disclosure is directed to peptides having antimicrobial activity and methods of using the peptides to inhibit microorganisms.

The disclosure provides synthetic antimicrobial agents having at least two 14 amino acid peptide sequences operably linked. The amino acid peptide sequence is generally the sequence of formula 1 (Gly-$X_1$-$X_2$-$X_3$-$X_1$-$X_1$-$X_1$-Arg-$X_4$-$X_1$-$X_5$-$X_6$-$X_6$-Gly) where $X_1$ is selected from the group of Leu or Ile; $X_2$ is selected from the group of Ala, Val, Leu, Ile, or Pro; $X_3$ is selected from the group of Arg or Trp; $X_4$ is selected from the group of Trp, Ile, or Leu; $X_5$ is selected from the group of Phe or Trp; and, $X_6$ is selected from the group of Phe, Trp, or Arg. In some aspects, the amino acid peptide sequence has at least 70% sequence identity to a sequence provided in SEQ ID NO: 3-33. In some aspects, the amino acid peptide sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least one sequence provided in SEQ ID NO: 3-33. Preferably, the amino acid peptide sequence has at least 85% sequence identity to SEQ ID NO: 8.

In some aspects, the antimicrobial agent disclosed includes a first synthetic amino acid sequence and a second synthetic amino acid sequence operably linked. Such second synthetic amino acid sequence, like the first synthetic amino acid sequence, is at least a 14 amino acid peptide sequence. Generally, the second synthetic amino acid sequence also has a sequence of formula 1 described above. In some aspects, the second synthetic amino acid sequence is identical to the first synthetic amino acid sequence, creating a homodimer. In other aspects, the second synthetic amino acid sequence is not identical to the first synthetic amino acid sequence, creating a heterodimer. In some aspects, the antimicrobial agent includes a sequence having at least 70% sequence identity to a sequence provided in SEQ ID NO: 40-4101. In some aspects, the antimicrobial agent includes a sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least one sequence provided in SEQ ID NO: 40-4101. Preferably, the antimicrobial agent includes a sequence having at least 85% sequence identity to SEQ ID NO: 40.

In some aspects, the antimicrobial agent of the disclosure includes a linker sequence that operably connects the first synthetic amino acid sequence to the second synthetic amino acid sequence. Suitable linker sequences further enhance kinetics of antimicrobial activity of the antimicrobial agent. In some aspects, the linker sequence is tailored to enhance solubility in polar environments. In some aspects, the linker sequence is tailored to enhance solubility in lipophilic environments. In some aspects, the linker sequence is tailored to enhance chemical stability in a variety of chemical environments. Suitable linker sequences may be 3, 4, 5, 6, 7, 8, 9, 10, 11, 12, 13, 14, 15, 16, 17, 18, 19, 20, or more amino acids in length. Preferably, the linker sequence is about 5, 6, 7, 8, 9, or 10 amino acids in length. More preferably, the linker sequence is about 5 to 8 amino acids in length. Suitable linker sequence may include any amino acid in each position, so long as the antimicrobial activity of the antimicrobial agent is not disrupted. Such linker sequences include those that permit antiparallel alignment of two distinct helices formed by the first synthetic and second synthetic amino acid sequences. Such linker sequences also include those that enhance antimicrobial activity of the first synthetic and second synthetic amino acid sequences. By way of example, without limitation, the first amino acid position of the linker sequence may be productively occupied with an anionic residue such as aspartate or glutamate, which may enhance antimicrobial activity by stabilizing an active conformation. Also, by way of example, without limitation, the linker sequence may include 5 to 8 asparagine residues to enhance solubility in polar environments while not disturbing the active conformation incumbent in the remainder of the molecule. Alternatively, the linker sequence may include 5 to 8 glycine residues to enhance solubility in polar environments while not disturbing the active conformation incumbent in the remainder of the molecule. In other aspects, the linker sequence may be of a heterogeneous form, composed of about 5 to about 8 residues selected from the following amino acids, including, asparagine, glutamine, glycine, histidine, serine, threonine, and combinations thereof. Suitable heterogeneous formulations may be selected to enhance solubility in polar environments while not disturbing the active conformation incumbent in the remainder of the molecule.

In some aspects, the linker sequence is generally the sequence of formula 2: (A1-P2-P3-. . . Pn), with "A" referring to an anionic residue, "P" referring to a polar residue, and "n" referring to an integer between about 3 and about 25. Suitable anionic residues include those known as such in the art, including, without limitation, aspartate and glutamate. Suitable polar residues include those known as such in the art, including, without limitation, glutamine, glycine, histidine, serine, and threonine. In some aspects, n is an integer such as that including, 3, 4, 5, 6, 7, 8, 9, 10, 11, 12, 13, 14, 15, 16, 17, 18, 19, 20, 21, 22, 23, 24, or 25. Preferably, n is an integer such as 5, 6, 7, 8, 9, 10, 11, 12, 13, 14, or 15. In some aspects, the linker sequence has at least 70% sequence identity to a sequence of formula 2. In some aspects, the amino acid sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a sequence of formula 2. Preferably, the linker sequence has at least 85% sequence identity to a sequence of formula 2.

In some aspects, the linker sequence has at least 70% sequence identity to a sequence provided in SEQ ID NO: 34-39. In some aspects, the amino acid sequence has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to at least one sequence provided in SEQ ID NO: 34-39. Preferably, the linker sequence has at least 85% sequence identity to at least one sequence provided in SEQ ID NO: 34-39.

The antimicrobial agents of the disclosure also include nucleic acid molecules encoding the amino acid sequences described herein, as well as expression vectors, encoding an antimicrobial agent, variant, or fragment thereof. Also, the disclosure provides isolated cells containing such nucleic acids, expression vectors, or peptides described herein. The disclosure provides compositions containing nucleic acid molecules or peptides of the disclosure, as well as variants or fragments thereof. Further, the disclosure provides articles of manufacture containing nucleic acid molecules or peptides of the disclosure, as well as variants or fragments thereof.

The disclosure provides antimicrobial agents having broad antimicrobial activity against microorganisms including bacteria, yeast, protozoa, fungi, mold, viruses, and combinations thereof. In some aspects, the antimicrobial agents have antimicrobial activity against Gram-positive and Gram-negative bacteria. The antimicrobial agents of the disclosure may be used to inhibit or prevent growth of a microorganism. Such microorganisms may include, without limitation, strains of *Pseudomonas, Escherichia, Staphylococcus, Streptococcus, Enterococcus, Mycobacteria, Haemophilus*, and combinations thereof.

In some aspects, the antimicrobial compositions may include a pharmaceutical carrier. In some aspects, the antimicrobial compositions may include a food additive.

The disclosure provides methods of reducing or inhibiting growth or survival of a microbe. Such methods include contacting the microbe with the antimicrobial agent.

In some aspects, the disclosure provides a method of reducing or inhibiting growth or survival of a microbe in a subject. The method includes contacting, or administering to, the subject a composition containing an antimicrobial agent. A therapeutically effective amount of the composition is delivered to the subject.

In some aspects, the disclosure provides a method of treating a microbial infection in a subject. The method includes contacting, or administering to, the subject a composition containing an antimicrobial agent disclosed herein. A therapeutically effective amount of the composition is delivered to the subject.

In some aspects, the disclosure provides a method of treating mastitis in a subject. The method includes identifying a subject having mastitis and contacting, or administering to, the subject a composition containing an antimicrobial agent. In some aspects, a therapeutically effective amount of the composition is administered directly to the mammary tissue of the subject.

The present disclosure further provides an article of manufacture, or kit, that includes a vessel and an antimicrobial agent. The article of manufacture may include packaging material that contains the antimicrobial agent and a label that indicates the antimicrobial agent can be used for treating mastitis. The article of manufacture may include packaging material that contains the antimicrobial agent and a label that indicates the antimicrobial agent can be used for treating a microbial infection in a subject. The article of manufacture may include packaging material that contains the antimicrobial agent and a label that indicates the antimicrobial agent can be used for inhibiting the growth or survival of microbes. The article of manufacture may include packaging material that contains the antimicrobial agent and a label that indicates the antimicrobial agent can be used for inhibiting the growth or survival of microbes in a subject.

BRIEF DESCRIPTION OF THE DRAWINGS

The following drawings form part of the present specification and are included to further demonstrate certain aspects of the disclosure. The disclosure may be better understood by reference to one or more of these drawings in combination with the detailed description of specific embodiments presented herein.

The patent or application file contains at least one drawing executed in color. Copies of this patent or patent application publication with color drawings will be provided by the Office upon request and payment of the necessary fee.

DETAILED DESCRIPTION

In accordance with the present disclosure, compositions and methods of using antimicrobial agents to inhibit the growth or survival of microorganisms have been discovered. In particular, antimicrobial agents having peptides with antimicrobial activity are used to inhibit the growth or survival of microorganisms. Therefore, the compositions and methods described herein are useful for antimicrobial treatments and therapeutics. Furthermore, the compositions and methods described herein may be used where antimicrobial resistance has reduced the availability of antimicrobial treatments or therapeutics.

I. Compositions

The compositions of the disclosure include antimicrobial agents having antimicrobial activity against at least one microorganism. In some aspects, the compositions of the disclosure include antimicrobial agents having antimicrobial activity against more than one microorganism.

a. Nucleic Acids Encoding Antimicrobial Agents

The disclosure provides antimicrobial agents that include synthetic peptides having antimicrobial activity. In some aspects the antimicrobial agents include peptides, a fragment thereof, or a variant thereof, as well as nucleic acid molecules that encode the synthetic peptide of the disclosure. Such nucleic acid molecules may include an expression vector.

Nucleic acids encoding antimicrobial peptides derived from water buffalo host defense proteins are disclosed. The nucleic acid sequences encoding antimicrobial peptides of the disclosure were derived from SEQ ID NO: 1 and the encoded amino acid sequence of SEQ ID NO: 2, having the antimicrobial peptide sequence of SEQ ID NO: 3. Suitable nucleotide sequences of the present disclosure include those that encode a peptide having antibacterial activity such as those peptides provided by SEQ ID NOs: 3-33, 40-4101, and those described herein.

Mutant nucleotides of the antimicrobial peptides may be used, so long as mutants include nucleic acid sequences that encode functional antimicrobial peptides as described herein. The subject nucleic acids may be mutated to alter properties of the encoded peptide such as expression properties, folding properties, solubility properties, and antibacterial activity. A skilled artisan will recognize that proteins encoded by nucleic acids encoding homologues or mutants may have the same antibacterial properties as the peptides of SEQ ID NOs: 3-33 and 40-4101, or may have altered antibacterial properties. The DNA sequence or protein product of such a mutation will usually be substantially similar to the sequences provided herein and will differ by one or more nucleotides or amino acids. The sequence changes may be substitutions, insertions, deletions, or a combination thereof. Techniques for mutagenesis of cloned genes are known in the art. Methods for site specific mutagenesis may be found in Gustin et al., Biotechniques 14:22, 1993; Barany, Gene 37:111-23, 1985; Colicelli et al., Mol. Gen. Genet. 199:537-9, 1985; and Sambrook et al., Molecular Cloning: A Laboratory Manual, CSH Press 1989, pp. 15.3-15.108 and all incorporated herein by reference. Such mutated nucleic acid derivatives may be used to study structure-function relationships of a particular antimicrobial peptide, or to alter properties of the peptide that affect its function or regulation. In summary, the disclosure relates to antimicrobial peptide coding sequences such as those that encode amino acid sequences of SEQ ID NOs: 3-33, 40-4101, and variants or mutants thereof. Also, the disclosure encompasses the intermediary RNAs encoded by the described nucleic acid sequences and that translates into an antimicrobial peptide of the disclosure.

b. Antimicrobial Peptide Compositions

A synthetic peptide disclosed herein may be obtained using methods known in the art, including isolation from a cell expressing the peptide, chemical synthesis, or the peptide may be expressed from a recombinant nucleic acid molecule. Methods of synthesizing a subject peptide are described in Current Protocols in Protein Science, Units 5, pub. John Wiley & Sons, Inc., 2002 and Current Protocols in Protein Science, Units 6, pub. John Wiley & Sons, Inc., 2002 and both are incorporated herein by reference.

The disclosure contemplates antimicrobial peptides and mutants thereof, which include those peptides encoded by the subject nucleic acids. The synthetic antibacterial peptides, or agents, disclosed herein are exemplified by the sequences of SEQ ID NOs: 3-33 and 40-4101. Further, the disclosure includes both homodimers and heterodimers of the antibacterial peptides described herein.

Homologs or peptides that vary in sequence from the amino acid sequences SEQ ID NOs: 3-33 and 40-4101 are also included in the disclosure. By homolog is meant a protein having at least about 10%, usually at least about 25%, 30%, 40%, 45%, 50%, 55%, 60%, 65%, 70%, 75%, 80%, 85%, 90%, 95%, 99% or higher amino acid sequence identity to the proteins encoded by SEQ ID NOs: 3-33 or 40-4101, as determined using MegAlign, DNAstar (1998) clustal algorithm as described in Higgins, D. G. and Sharp, P. M., Fast and Sensitive Multiple Sequence Alignments on a Microcomputer, CABIOS, 5: 151-153, 1989, both incorporated herein by reference.

Antimicrobial peptides disclosed herein may be mutated, or altered, to enhance, or change, biological properties of the protein. Such biological properties include, but are not limited to, in vivo or in vitro stability (e.g., half-life), solubility, amphiphilicity and various aspects of antimicrobial activity. Such antimicrobial activity aspects include, without limitation, tissue specificity, microbial target selectivity, broad spectrum antimicrobial potency and invariance as a function of microbial resistance mechanisms. Suitable mutations include single amino acid changes, deletions of one or more amino acids, N-terminal truncations, C-terminal truncations, insertions, etc. Mutants can be generated using standard techniques of molecular biology, including random mutagenesis and targeted mutagenesis as described in Current Protocols in Molecular Biology, Unit 8, pub, John Wiley & Sons, Inc., 2000 and incorporated herein by reference.

The manifold of currently considered peptide formulations is of substantial value because the manifold as a whole has a mechanism of action that is not susceptible to a key microbial antioxidative resistance mechanism conferred by membrane expression of staphyloxanthin. Furthermore, strategic sequence variation within the manifold may be applied to counteract microbial defenses effected by adaptive membrane charge distribution corresponding to covalent modification of anionic lipids, or greater membrane staphyloxanthin expression.

The antimicrobial peptides disclosed herein are characterized by having antimicrobial activity. Specifically, the peptides disclosed are capable of disrupting the cell membrane of microorganisms, leading to the microorganism's destruction.

The antimicrobial peptides generally have a first synthetic amino acid sequence of formula 1 (Gly-$X_1$-$X_2$-$X_3$-$X_1$-$X_1$-$X_1$-Arg-$X_4$-$X_1$-$X_5$-$X_6$-$X_6$-Gly) where $X_1$ is selected from the group of Leu or Ile; $X_2$ is selected from the group of Ala, Val, Leu, Ile, or Pro; $X_3$ is selected from the group of Arg or Trp; $X_4$ is selected from the group of Trp, Ile, or Leu; $X_5$ is selected from the group of Phe or Trp; and, $X_6$ is selected from the group of Phe, Trp, or Arg.

The antimicrobial peptides also may have a second antimicrobial synthetic amino acid sequence of formula 1 (Gly-$X_1$-$X_2$-$X_3$-$X_1$-$X_1$-$X_1$-Arg-$X_4$-$X_1$-$X_5$-$X_6$-$X_6$-Gly) where $X_1$ is selected from the group of Leu or Ile; $X_2$ is selected from the group of Ala, Val, Leu, Ile, or Pro; $X_3$ is selected from the group of Arg or Trp; $X_4$ is selected from the group of Trp, Ile, or Leu; $X_5$ is selected from the group of Phe or Trp; and, $X_6$ is selected from the group of Phe, Trp, or Arg. The antimicrobial agent may include a homodimer of antimicrobial peptides, where a first antimicrobial synthetic sequence has the same sequence as a second antimicrobial synthetic sequence. The antimicrobial agent may include a heterodimer of antimicrobial peptides, where a first antimicrobial synthetic sequence has a different sequence as a second antimicrobial synthetic sequence. Such difference may be by one or more amino acid sequences.

The antimicrobial peptides typically range in length from about 14 amino acid residues to about 30 amino acid residues. In some aspects, the antimicrobial peptides are about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or more amino acid residues in length. Preferably, the antimicrobial peptides are 14 amino acid residues in length. In some aspects, antimicrobial agents including homodimers of the antimicrobial peptides are about 28 amino acid residues in length. In some aspects, antimicrobial agents including homodimers of the antimicrobial peptides are about 35 amino acid residues in length. In some aspects, antimicrobial agents including heterodimers of the antimicrobial peptides are about 28 amino acid residues in length. In some aspects, antimicrobial agents including heterodimers of the antimicrobial peptides are about 35 amino acid residues in length. A skilled artisan will recognize that the length of a homodimer or heterodimer of the antimicrobial peptides depends upon the length of the antimicrobial peptide used in the respective homodimer or heterodimer.

The antimicrobial agent may include a linker sequence to connect a first antimicrobial synthetic sequence to a second antimicrobial synthetic sequence. In some aspects, the linker sequence connected to a first and second antimicrobial peptide produces a covalently linked dimer formulation. Suitable linker sequences may be used to improve antimicrobial kinetics. In one aspect, the linker sequence enhances kinetics by encouraging the dimerized structure to remain in a conformation conducive to antimicrobial activity. In one aspect, the linker sequence may be used to enhance delivery of the dimer. Such linker sequences may include specific amino acid formulations that favor solubility in polar or lipophilic media. In another aspect, the linker sequence may be used to enhance chemical stability within different environments.

Suitable linker sequences may be tailored to provide specific enhancements. A linker sequence may be a length of any size that does not disrupt the antimicrobial activity of the antimicrobial peptide. In some aspects, the linker sequence may be a length of about 2, 3, 4, 5, 6, 7, 8, 9, 10, 11, 12, 13, 14, 15, 16, 17, 18, 19, 20, 25, 30, 35, 40, 45, 50 or more amino acid residues. Preferably, the linker sequence is a length of about 2, 3, 4, 5, 6, 7, 8, 9, or 10 amino acid residues. In some aspects, the linker sequence is a length of about 7 amino acid residues. The amino acid residues of the linker sequence may be tailored to provide specific enhancements. In some aspects, the linker sequence includes mostly polar amino acids. In some aspects, the linker sequence includes at least one sequence of SEQ ID NO: 34-39. In some aspects, the linker sequence includes the sequence of SEQ ID NO: 34.

c. Pharmaceutical Compositions

The present disclosure provides a pharmaceutical composition including at least one antimicrobial agent described herein. To prepare such a pharmaceutical composition, an antimicrobial agent, an antimicrobial peptide, homodimer, heterodimer, or combinations thereof is synthesized or otherwise obtained, purified as necessary or desired and then lyophilized and stabilized. The antimicrobial agent may then be adjusted to the appropriate concentration and combined with other agents or pharmaceutically acceptable carriers. Suitable pharmaceutically acceptable carriers include, without limitation, a carrier, diluent, excipient, salt, or combinations thereof, that are compatible with the other ingredients of the formulation and not deleterious to the recipient thereof.

Pharmaceutical formulations containing an antimicrobial agent disclosed herein may be prepared by procedures known in the art using well-known and readily available ingredients. For example, the antimicrobial agent may be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents may also be included such as carboxymethyl cellulose, hydroxymethylcellulose, hydroxypropyl methylcellulose and other cellulose derivatives, alginates, gelatin, and polyvinyl-pyrrolidone.

II. Methods

The compositions of the present disclosure including at least one antimicrobial agent are useful in methods of reducing the growth or survival of microorganisms. A skilled artisan will appreciate the numerous methods of using the antimicrobial agents disclosed herein. Accordingly, the methods included herein are examples and are not limiting of the scope by which the antimicrobial agents may be used. The methods of the disclosure include reducing the growth or survival of microorganisms, treating a subject having a microorganism infection, and treating a subject having mastitis, as well as other methods using the antimicrobial agents disclosed herein.

Microorganisms against which an antimicrobial agent disclosed herein is active include Gram-negative bacteria, Gram-positive bacteria, yeast, fungi, mold, viruses, unicellular parasites, and other microorganisms known in the art. Non-limiting examples include *Staphylococcus aureus, Listeria monocytogenes, Escherichia coli, Klebsiella pneumoniae, Salmonella typhimurium, Pseudomonas aeruginosa, Proteus mirabilis, Salmonella enteritidis, Neisseria gonorrhoeae, Ureaplasma canigenitalium, Ureaplasma urealyticum, Candida albicans, Trichomonas vaginalis, Treponema pallidum, Chlamydia trachomatis, Staphylococcus hyicus, Coagulase negative staphylococci, Streptococcus agalactiae, Streptococcus hyicus, Streptococcus epidermidis, Streptococcus xylosus, Streptococcus intermedius. Streptococcus* dysgalactiae, Streptococcus uberis, Mycoplasma spp. (*Mycoplasma bovis, Mycoplasma bovigenitalium, Mycoplasma canadense, Mycoplasma californicum, Mycoplasma alkalescens*), *Escherichia coli, Klebsiella* spp. (*Klebsiella pneumoniae, Klebsiella oxytoca*), *Enterobacter* spp. (*E. aerogenes, E. amnigenus, E. agglomerans, E. arachidis, E. asburiae, E. cancerogenous, E. cloacae, E. cowanii, E. dissolvens, E. gergoviae, E. helveticus, E. hormaechei, E. intermedius, E. kobei, E. ludwigii, E. mori, E. nimipressuralis, E. oryzae, E. pulveris, E. pyrinus, E. radicincitans, E. taylorae, E. turicensis, E. sakazakii, Enterobacter soli*), *Citrobacter* spp (*C. amalonaticus, C. braakii, C. diversus, C. farmeri, C. freundii, C. gillenii, C. koseri, C. murliniae, C. rodentium, C. sedlakii, C. werkmanii, C. youngae*), *Proteus* spp. (*P. hauseri, P. mirabilis, P. myxofaciens, P. penneri, P. vulgaris*), Enterococci, *Serratia* spp., *Pseudomonas* spp. (*P. aeruginosa, P. alcaligenes, P. anguilliseptica, P. argentinensis, P. borbori, P. citronellolis, P. flavescens, P. mendocina, P. nitroreducens, P. oleovorans, P. pseudoalcaligenes, P. resinovorans, P. straminea*), *P. chlororaphis* group (*P. agarici, P. asplenii, P. aurantiaca, P. aureofaciens, P. chlororaphis, P. corrugata, P. fragi, P. lundensis, P. taetrolens*), *P. fluorescens* group (*P. antarctica, P. azotoformans, P. brassicacearum, P. brenneri, P. cedrina, P. corrugata, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii*), *P. pertucinogena* group (*P. denitrificans, P. pertucinogena*), *P. putida* group (*P. cremoricolorata, P. fulva, P. monteilii, P. mosselii, P. oryzihabitans, P. parafulva, P. plecoglossicida, P. putida*), *P. stutzeri* group (*P. balearica P. luteola, P. stutzeri*), *P. syringae* group (*P. amygdali, P. avellanae, P. caricapapayae, P. cichorii, P. coronafaciens, P. ficuserectae, P. meliae, P. savastanoi, P. syringae, P. viridiflava*), incertae sedis (*P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophila, P. psychrotolerans, P. rathonis, P. reptilivora, P. resiniphila, P. rhizosphaerae, P. rubescens, P. salomonii, P. segitis, P. septica, P. simiae, P. suis, P. thermotolerans, P. tremae, P. trivialis, P. turbinellae, P. tuticorinensis, P. umsongensis, P. vancouverensis, P. vranovensis, P. xanthomarina*), Prototheca, Corynebacterium bovis, Arcanobacterium pyogenes, *Bacillus* spp. (*B. alcalophilus, B. alvei, B. aminovorans, B. amyloliquefaciens, B. aneurinolyticus, B. anthracis, B. aquaemaris, B. atrophaeus, B. azotoformans, B. badius, B. boroniphilus, B. brevis, B. caldolyticus, B. centrosporus, B. cereus, B. circulans, B. coagulans, B. fastidious, B. firmus, B. flavothermus, B. fusiformis, B. galliciensis, B. globigii, B. globisporus, B. infernus, B. insolitus, B. larvae, B. laterosporus, B. lentimorbus, B. lentus, B. licheniformis, B. macerans, B. macquariensis, B. marinus, B. megaterium, B. mesentericus, B. mucilaginosus, B. mycoides, B. natto, B. pantothenticus, B. pasteurii, B. polymyxa, B. popilliae, B. pseudoanthracis, B. pumilus, B. schlegelii, B. sphaericus, B. sporothermodurans, B. stearothermophilus, B. subtilis, B. thuringiensis, B. vulgatis, B. weihenstephanensis*), *Pasteurella* spp. (*P. aerogenes, P. anatis, P. avium, P. bettyae, P. caballi, P. canis, P. dagmatis, P. gallicida, P. gallinarum, P. granulomatis, P. langaaensis, P. lymphangitidis, P. mairii, P. multocida, P. oralis, P. pneumotropica, P. skyensis, P. stomatis, P. testudinis, P. trehalosi, P. ureae, P. volantium*), *Serratia* spp. (*S. entomophila, S. ficaria, S. fonticola, S. grimesii, S. liquefaciens, S. marcescens, S. odorifera, S. plymuthica, S. proteamaculans, S. quinivorans, S. rubidaea, S. symbiotica*), and other microorganisms known in the art. Such unicellular parasites include, without limitation, leishmania, treponema, giardia, and others known in the art.

In some aspects, microorganisms against which an antimicrobial agent disclosed herein is active may also include medically relevant bacteria. Such medically relevant bacteria may include, without limitation, Staphylococcus aureus, S. epidermidis, S. haemolyticus, S. intermedius, S. lugdunensis, S. saprophiticus, S. schleiferi, S. warneri; Streptococcus agalactiae, S. anginosus, S. bovis, S. equisimilis, S. mitis, S. mutans, S. pneumonia, S. pyogenes, S. sanguis, S. salivarius, S. suis; Enterococcus faecalis, E. faecium; Neisseria gonorrhoeae, N. meningitides; Moraxella catarrhalis, M. lacunata, M. nonliquefaciens, M. urethralis; Kingella kingae, K. denitrificans; Eikenella corrodens; Bacillus alvei, B. anthracis, B. brevis, B. cereus, B. circulans, B. coagulans, B. licheniformis, B. macerans, B. pumilus, B. sphaericus, B. subtilis, B. thuringiensis; Clostridium botulinum, C. bifermentans, C. butyricum, C. camis, C. clostridioforme, C. difficile, C. fallax, C. histolyticum, C. innocuum, C. perfringens, C. novyi, C. ramosum, C. septicum, C. sordellii, C. tertium, C. tetani; Listeria monocytogenes; Erysipelothrix rhusiopathiae; Propionibacterium acnes, Streptobacillus moniliformis; Calymmatobacterium granulomatis; Bacteroides distasonis, B. fragilis, B. thetaiotaomicron, B. ovatus, B. vulgatus; Fusobacterium mortiferum, F. nucleatum, F. necrophorum; Gemella morbillorum; Peptostreptococcus (P. anaerobius, P. asaccharolyticus, P. hydrogenalis, P. magnus, P. melaminogenica, P. micros, P. tetradius, P. prevotii,); Porphyromonas (P. asaccharolytica, P. gingivalis); Prevotella (P. melaminogenica, P. oris, P. buccae); Veillonella parvula; Salmonella choleraesuis, S. enteritidis, S. gastroenteritis, S. paratyphi-A, S. schottmuelleri, S. typhi, S. typhimurium; Shigella boydii, S. dysenteriae, S. flexneri, S. sonnei; Arcobacter cryaerophilia, A. butzleri, A. skirrowii; Campylobacter coli, C. fetus, C. hyointestinalis, C. jejuni, C. lad, C. sputorum, C. upsaliensis; Helicobacter pylori, H. cinaedi, H. fennelliae; Vibrio cholera, V. damsela, V. fetus, V. fluvialis, V. furnissia, V. hollisae, V. mimicus, V. parahaemolyticus, V. vulnificus; Citrobacter freundii, C. diversus (C. koseri); Escherichia coli; Enterobacter aerogenes, E. cloacae; Klebsiella pneumoniae, K. rhinoscleromatis, K. ozaenae; Proteus mirabilis; Serratia marcescens; Pseudomonas aeruginosa, P. cepacia, P. fluorescens, P. maltophilia, P. mallei, P. pseudomallei, P. putida, P. putrefaciens, P. stutzeri; Brucella abortus, B. canis, B. melitensis, B. suis; Pasteurella haemolytica, P. multicida; Yersinia enterocolitica, Y. pestis, Y. pseudotuberculosis; Francisella tularensis; Haemophilus influenza, H. parainfluenzae, H. ducreyi, H. aegyptius; Bordetella avium, B. bronchiseptica, B. hinzii, B. parapertussis, B. pertussis; Corynebacterium diphtheria, C. kutscheri, C. pseudotuberculosis, C. pseudodiphtheriticum, C. renale, C. xerosis, C. ulcerans; Mycobacterium africanum, M. avium-intracellulare, M. bovis, M. fortuitum, M. kansasii, M. leprae, M. marinum, M. microtii, M. tuberculosis, M. scrofulaceum, M. ulcerans; Nocardia asteroides, N. brasiliensis, N. caviae; Actinomyces bernardiae, A. bovis, A. denticolens, A. gerencseriae, A. georgiae, A. hordeovulneris, A. howellii, A. hyovaginalis, A. israelii, A. meyeri, A. naeslundii, A. neuii, A. odontolyticus, A. pyogenes, A. radingae, A. slackii, A. suis, A. turicensis, A. viscosus; Propionibacterium propionicus; Streptomyces somaliensis; Leptospira interrogans, L. biflexa, Borrelia burgdorferi; B. hermsii, B. recurrentis, B. turicatae; Spirillum minum; Treponema pallidum, *T. carateum*; *Mycoplasma fermentans, M. genitalium, M. hominis, M. penetrans, M. pirum, M. pneumonia*; *Ureaplasma urealyticum*; *Rickettsiae akari, R. australis, R. conorii, R. japonica, R. prowazekii, R. rickettsii, R. sibirica, R. typhi*; *Ehrlichia canis, E. chaffeensis, E. equi, E. ewingii, E. phagocytophila, E. platys, E. risticii, E. sennetsu*; *Orientia tsutsugamushi*; *Coxiella burnetii*; *Bartonella bacilliformis*; *B. henselae, B. Quintana*; *Chlamydia pneumonia, C. psittaci, C. trachomatis*; *Legionella ansia, L. dumollii, L. feelei, L. micdadei, L. pneumophila*, and other medically relevant bacteria known in the art or yet to be discovered.

In some aspects, microorganisms against which an antimicrobial agent disclosed herein is active may also include veterinary relevant bacteria. Such relevant bacteria may include, without limitation, *Acholeplasma laidlawii*; *Acinetobacter lwoffii*; *Actinobacillus equuli, A. lignieresii, A. pleuropneumoniae, A. rossi, A. suis*; *Actinobaculum suis*; *Actinomyces bovis, A. viscosus*; *Aeromonas hydrophila, A. salmonicida*; *Aliivibrio salmonicida*; *Anaplasma phagocytophilum*; *Arcobacter butzleri*; *Avibacterium paragallinarum*; *Bacillus anthracis, B. cereus, B. licheniformis, B. subtilis, B. thuringiensis*; *Bacteroides fragilis*; *Bartonella clarridgeiae, B. elizabethae, B. henselae, B. vinsonii*; *Bibersteinia trehalosi*; *B. avium, B. bronchiseptica, B. parapertussis, B. pertussis*; *Borrelia afzelii, B. anserine, B. burgdorferi, B. garinii*; *Brachyspira aalborgi, B. alvinipulli, B. hyodysenteriae, B. intermedia, B. pilosicoli, B. suanatina*; *Brochothrix thermosphacta*; *Brucella abortus, B. canis, B. ceti, B. melitensis, B. ovis, B. pinnipedialis, B. suis*; *Burkholderia mallei, B. pseudomallei*; *Campylobacter coli, C. fetus, C. jejuni, C. lad, C. upsaliensis*; *Chlamydia trachomatis*; *Chlamydophila abortus, C. felis, C. psittaci*; *Citrobacter freundii*; *Clostridium botulinum*, group I, II, III, IV; *Clostridium chauvoei, C. difficile, C. haemolyticum, C. novyi, C. perfringens, C. piliforme, C. septicum, C. sordellii, C. tetani*; *Corynebacterium bovis, C. diphtheria, C. kutscheri, C. pseudotuberculosis, C. renale, C. ulcerans*; *Coxiella burnetii*; *Dermatophilus congolensis*; *Dichelobacter nodosus*; *Edwardsiella ictaluri, E. tarda*; *Ehrlichia canis, E. ruminantium*; *Enterococcus faecalis, E. faecium*; *Erysipelothrix rhusiopathiae*; *Escherichia coli*; *Flavobacterium columnare, F. psychrophilum*; *Francisella noatunensis, F. tularensis*; *Fusobacterium canifelinum, F. equinum, F. necrophorum*; *Gallibacterium anatis*; *Haemophilus parasuis*; *Helicobacter hepaticus, H. pylori*; *Histophilus somni*; *Klebsiella oxytoca, K. pneumoniae*; *Lactobacillus plantarum*; *Lawsonia intracellularis*; *Legionella pneumophila*; *Leptospira borgpetersenii, L. interrogans, L. kirschneri*; *Listeria innocu, L. ivanovii, L. monocytogenes*; *Listonella anguillarum*; *Mannheimia granulomatis, M. haemolytica, M. varigen*; *Melissococcus plutonius*; *Microcystis aeruginosa*; *Moraxella bovis, M. osloensis*; *Morganella morganii*; *Mycobacterium avium, M. bovis, M. leprae, M. marinum, M. tuberculosis*; *Mycoplasma agalactiae, M. bovis, M. capricolum, M. felis, M. gallisepticu, M. haemofelis, M. hyopneumoniae, M. hyorhinis, M. hyosynoviae, M. meleagridi, M. mycoides, M. pneumonia, M. pulmonis, M. suis, M. synoviae*; *Neisseria gonorrhoeae*; *Neorickettsia risticii*; *Nicoletella semolina*; *Nocardia asteroids*; *Paenibacillus larvae*; *Pasteurella caballi, P. dagmatis, P. multocida, P. pneumotropica*; *Peptoniphilus indolicus*; *Plesiomonas shigelloides*; *Prevotella melaminogenica*; *Proteus mirabilis, P. vulgaris*; *Pseudomonas aeruginosa, P. anguilliseptica*; *Renibacterium salmoninarum*; *Rhodococcus equi*; *Rickettsia prowazekii, R. rickettsia*; *Riemerella anatipestifer*; *Salmonella* spp., *S. enterica*; *Serratia marcescens*; *Shigella dysenteriae, S. flexneri*; *Staphylococcus aureus, S. epidermidis, S. felis, S. hyicus, S. intermedius, S. pseudintermedius, S. schleiferi*; *Stenotrophomonas maltophilia*; *Streptobacillus moniliformis*; *Streptococcus agalactiae*; *S. canis, S. devriesei, S. dysgalactiae, S. equi, S. pneumonia, S. porcinus, S. pyogenes, S. suis, S. uberis*; *Taylorella asinigenitalis, T. equigenitalis*; *Treponema pallidum, T. paraluiscuniculi, T. pedis, T. phagedenis*; *Trueperella pyogenes*; *Ureaplasma diversum*; *Vibrio alginolyticus, V. cholera, V. parahaemolyticus, V. vulnificus*; *Yersinia enterocolitica, Y. pestis, Y. pseudotuberculosis, Y. ruckeri* and other veterinary relevant bacteria known in the art or yet to be discovered.

The method of reducing the growth or survival of microorganisms includes contacting a microorganism population with an antimicrobial agent of the present disclosure. The method may include first identifying a microorganism population.

The methods disclosed herein include methods of inhibiting the survival or growth of a microorganism. The term "inhibit" includes a decrease in any detectable amount, for example, 5%, 10%, 20%, 30%, 40%, 50%, 60%, 70%, 80%, 90% or more, and can be determined by methods known in the art. Exemplary methods of detecting inhibition includes a determination by count, such as a bacterial culture or viral titer, or by evaluation of one or more symptoms associated with infection by a microorganism. Symptoms associated with infection by a microorganism are known in the art. Such symptoms are characteristic to a particular infectious microorganism and the resulting condition.

A composition that can support growth or survival of a microorganism may be contacted with an effective amount of the antimicrobial agent in a variety of ways. For example, if the composition is a food item, the antimicrobial agent may be added directly to the food, it may be incorporated into the matrix of the packaging material or it may be coated onto the packaging material, in which case the antimicrobial agent may be released during storage, upon dissolution of the encapsulation material, contact with moisture or at a predetermined temperature. If the composition is a body fluid, the antimicrobial agent may be added directly to the body fluid.

A subject may be contacted with the antimicrobial agent in a variety of ways including, without limitation, administration using routes commonly known in the art. Such routes include oral, parenteral (including subcutaneous, intravenous, intramuscular and intraperitoneal), rectal, vaginal, dermal, transdermal (topical), transmucosal, intrathoracic, intrapulmonary and intranasal (respiratory) routes. The means of administration may be by injection, using a pump or any other appropriate mechanism.

An antimicrobial agent disclosed herein may be administered to a subject in a single does, in multiple doses, in a continuous or intermittent manner, depending, for example, upon the recipient's physiological condition, whether the purpose of the administration is therapeutic or prophylactic, and other factors known to skilled artisans. The administration of the antimicrobial agents may be essentially continuous over a pre-selected period of time or may be in a series of spaced doses. Both local and systemic administration is contemplated.

The dosage to be administered to a subject may be any amount appropriate to reduce or prevent infection or to treat at least one symptom associated with the infection. Some factors that determine appropriate dosages are well known to those skilled in the art and may be addressed with routine experimentation. For example, determination of the physicochemical, toxicological and pharmacokinetic properties may be made using standard chemical and biological assays and through the use of mathematical modeling techniques known in the chemical, pharmacological and toxicological arts. The therapeutic utility and dosing regimen may be extrapolated from the results of such techniques and through the use of appropriate pharmacokinetic and pharmacodynamic models. Other factors will depend on individual patient parameters including age, physical condition, size, weight, the condition being treated, the severity of the condition, and any concurrent treatment. The dosage will also depend on the agent chosen and whether prevention or treatment is to be achieved, and if the agent is chemically modified.

The precise amount to be administered to a subject will be the responsibility of the attending physician. However, to achieve the desired effects, an antimicrobial agent disclosed herein may be administered as single or divided dosages. For example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results.

The absolute weight of a given antimicrobial agent disclosed herein included in a unit dose may vary widely. For example, about 0.01 to about 2 g, or about 0.1 to about 500 mg, of at least one antimicrobial agent may be administered. Alternatively, the unit dosage may vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the antimicrobial agents may vary as well. Such daily doses may range, for example, from about 0.1 g/day to about 50 g/day, from about 0.01 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

An antimicrobial agent may be used alone or in combination with a second medicament. The second medicament may be a known antimicrobial agent such as, but not limited to, a β-lactam, macrolide or other antibiotics, e.g. Azithromycin, Doxycycline, Tetracycline, and Erythromycin; an antifungal agent such as clotrimazole, nystatin, fluconazole, ketoconazole, amphotericin B, caspofungin, or voriconazole; an agent effective against a protozoan such as, for example, Metronidazole or timidazole. The second medicament may also be an antiviral agent such as Abacavir, Acyclovir, Amantadine, Didanosine, Emtricitabine, Enfuvirtide, Entecavir, Ganciclovir, Gardasil, Lamivudine, Nevirapine, Nelfinavir, Oseltamivir, Ribavirin, Rimantadine, Ritonavir, Stavudine, Valaciclovir, Vidarabine, Zalcitabine, and Zidovudine. The effective amount of the second medicament will follow the recommendations of the second medicament manufacturer, the judgment of the attending physician and will be guided by protocols and administrative factors for amounts and dosing as indicated in the PHYSICIAN'S DESK REFERENCE (as commonly known in the art).

The effectiveness of the method of treatment may be assessed by monitoring the subject for signs or symptoms of the microbial infection as discussed above, as well as determining the presence or amount of microorganism present in the subject by methods known in the art.

III. Kits

The present disclosure provides articles of manufacture and kits containing materials useful for treating the conditions described herein. The article of manufacture may include a container of a composition as described herein with a label. Suitable containers include, for example, bottles, vials, and test tubes. The containers may be formed from a variety of materials such as glass or plastic. The container holds a composition having an antimicrobial agent disclosed herein, which is effective for inhibiting the growth of a microorganism or treating a condition caused by a microorganism. The label on the container may indicate that the composition is useful for treating specific conditions and may also indicate directions for administration.

DEFINITIONS

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, "administering" is used in its broadest sense to mean contacting a subject with a composition disclosed herein.

As used herein, the term "antimicrobial activity" means microbicidal or microbiostatic activity or a combination thereof, against one or more microorganisms. Microbicidal activity refers to the ability to kill or cause irreversible damage to a target microorganism. Microbiostatic activity refers to the ability to inhibit the growth or proliferative ability of a target microorganism without necessarily killing or irreversibly damaging it.

As used herein, the term "identity" or "sequence identity" refers to a relationship between two or more polypeptide sequences, as well as two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis. For example, the sequences are "identical" at a particular position if at that position, the nucleotides or amino acid residues are identical. The total number of such position identities is then divided by the total number of nucleotides or residues in the reference sequence to give percent (%) sequence identity. Sequence identity can be readily calculated by known methods, including but not limited to, those described in Computational Molecular Biology, Lesk, A. N., et., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo et al., Applied Math., 48:1073 (1988), the teachings of which are incorporated herein by reference.

As used herein, the term "inhibit" means a decrease in any amount including, without limitation, a 5%, 10%, 15%, 20%, 25%, 30%, 35%, 40%, 45%, 50%, 55%, 60%, 65%, 70%, 75%, 80%, 85%, 90%, 95%, 100%.

The term "nucleic acid" is used herein to refer to a polymer of deoxynucleic ribose nucleic acids, as well as ribose nucleic acids. The term includes linear molecules, as well as covalently closed circular molecules. It includes single stranded molecules, as well as double stranded molecules.

As used herein, "subject" refers to a living organism having a central nervous system. In particular, subjects include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific values (e.g., captive or free specimens of endangered species), or mammals that otherwise have value. Suitable subjects also include: mice, rats, dogs, cats, ungulates such as cattle, swine, sheep, horses, and goats, lagomorphs such as rabbits and hares, other rodents, and primates such as monkeys and apes. In some aspects, subjects may be diagnosed with a microbial infection, may be at risk for a microbial infection, or may be experiencing a microbial infection. Subjects may be of any age including new born, adolescence, adult, middle age, or elderly.

The phrase "therapeutically effective amount" is used herein to mean an amount sufficient to increase to some beneficial degree, preferably to increase by at least about 1 to 100 percent, more preferably by at least about 5 to 95 percent, and more preferably by at least 8 percent or higher, healing or infection improvement as compared to untreated controls. An "effective amount" is a pharmaceutically-effective amount that is intended to qualify the amount of an agent or compound, that when administered to a subject, will achieve the goal of healing an infection site, inhibiting the growth of a microorganism, or otherwise benefiting the recipient environment.

The term "variant" relates to nucleotide or amino acid sequences which have similar sequences and that function in the same way.

Amino acid designations may include full name, three-letter, or single-letter designations as commonly understood by one of ordinary skill in the art to which this disclosure belongs.

As various changes could be made in the above compositions and methods without departing from the scope of the disclosure, it is intended that all matter contained in the above description and in the Examples given below, shall be interpreted as illustrative and not in a limiting sense.

EXAMPLES

Example 1

Antimicrobial Activity of Antimicrobial Agents

The antimicrobial agents disclosed are derivatives of SEQ. ID. NO.: 3, having 14 amino acids and a broad spectrum of antimicrobial activity. The antimicrobial agents of the disclosure were synthesized and analyzed to evaluate antimicrobial activity. Initially, the antimicrobial agent of SEQ ID NO.: 3 was evaluated for inhibition of clinical isolates of common mastitis pathogens (Table 1).

TABLE 1

Antimicrobial activity of the antimicrobial agent of SEQ ID NO.: 3 expressed as minimum inhibitory concentration (MIC).

| Clinical pathogen isolate | MIC (µM) | Bacteria strain |
|---|---|---|
| 335 B-S | 12.5 | *Streptococcus dysgalactiae* |
| 335 B-15 | 25.0 | *Klebsiella pneumoniae* |
| 404 C-18 | 12.5 | *Corynebacterium species* |
| 416 B-10 | 25.0 | *Staphylococcus aureus* |
| 331 C-10 | 25.0 | *Staphylococcus aureus* |
| 422 C-10 | 25.0 | *Staphylococcus aureus* |

Additional antimicrobial agents were evaluated for antimicrobial activity, including 23 computationally-derived analogues of SEQ ID NO: 3. These analogues were grouped into two functional series, including those synthesized for improved helicity (Table 2; A-P) and those synthesized for enhanced activity (Table 2; IND, Q-T, and W-X). The antimicrobial activity of the synthetic analogues provided in Table 2 were evaluated using standard techniques such as those described in Sang, et al. 2007 Dev. Comp. Immunol., and herein incorporated by reference. Based on the data collected, three synthetic antimicrobial agents were identified (Table 2, shaded rows) as having superior antimicrobial activity compared to the agent of SEQ ID NO: 3 or SEQ ID NO: 19 (Table 2).

TABLE 2

Antimicrobial activity of analogs against *Staphylococcus aureus* expressed as minimum inhibitory concentration (MIC).

| Peptide | Helicity Score | MW | MIC |
|---|---|---|---|
| A (SEQ ID NO: 3) | 3.64 | 1774.8 | 16.0 |
| B (SEQ ID NO: 4) | 11.12 | 1748.84 | 64.0 |
| C (SEQ ID NO: 5) | 14.39 | 1776.22 | >256.0 |
| D (SEQ ID NO: 6) | 20.37 | 1790.25 | >256.0 |
| E (SEQ ID NO: 7) | 3.72 | 1744.18 | 256.0 |
| F (SEQ ID NO: 8) | 13.13 | 1718.14 | 8.0 |
| G (SEQ ID NO: 9) | 16.91 | 1746.19 | 16.0 |
| H (SEQ ID NO: 10) | 23.70 | 1760.22 | 16.0 |
| I (SEQ ID NO: 11) | 3.12 | 1774.21 | 16.0 |
| J (SEQ ID NO: 12) | 9.80 | 1748.17 | >256.0 |
| K (SEQ ID NO: 13) | 12.75 | 1776.22 | >256.0 |
| L (SEQ ID NO: 14) | 18.22 | 1790.25 | >256.0 |
| M (SEQ ID NO: 15) | 3.15 | 1744.28 | >256.0 |
| N (SEQ ID NO: 16) | 11.47 | 1718.14 | 4.0 |
| O (SEQ ID NO: 17) | 14.84 | 1746.19 | 4.0 |
| P (SEQ ID NO: 18) | 18.73 | 1760.22 | 64.0 |
| IND (SEQ ID NO: 19) | 3.64 | 1901.27 | 64.0 |
| Q (SEQ ID NO: 20) | 0.17 | 1758.16 | >256.0 |
| R (SEQ ID NO: 21) | 13.2 | 1783.22 | 32.0 |
| S (SEQ ID NO: 22) | 21.7 | 1767.17 | 256.0 |
| T (SEQ ID NO: 23) | 11.7 | 1831.22 | >256.0 |
| W (SEQ ID NO: 24) | 5.0 | 1788.19 | >256.0 |
| X (SEQ ID NO: 25) | 6.2 | 1797.20 | >256.0 |

Example 2

Structural/Function Analysis of Antimicrobial Agents

The structure/function mechanisms for the antimicrobial agents described herein were evaluated. In order to develop a better understanding of the effects of different amino acids at different positions as well as developing the most biologically active and stable synthetic peptide(s), Quantitative Structure-Activity Relationship (QSAR) modeling was used to guide the optimization of multi-drug resistant *Staphyloccocus aureus* antimicrobial formulations.

Figure 5:
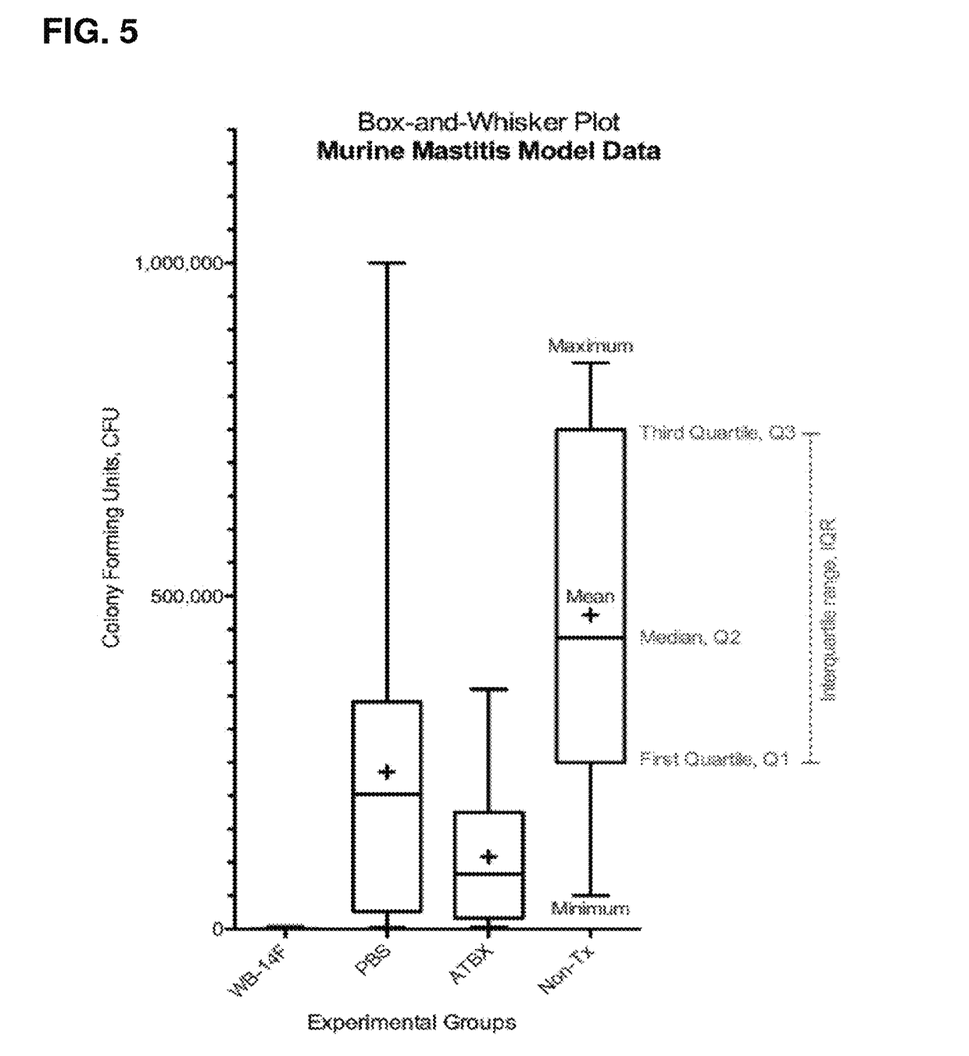
FIG. 5 graphically illustrates the antibiotic activity of the antimicrobial peptides of the disclosure. A statistically significant difference (P<0.001) was found between the groups (box-plot below), with the post-hoc test showing a difference between the WB-14F versus the three control groups (PBS, ATBX, and Non-Tx) at a 5% level of significance.
Figure 6:
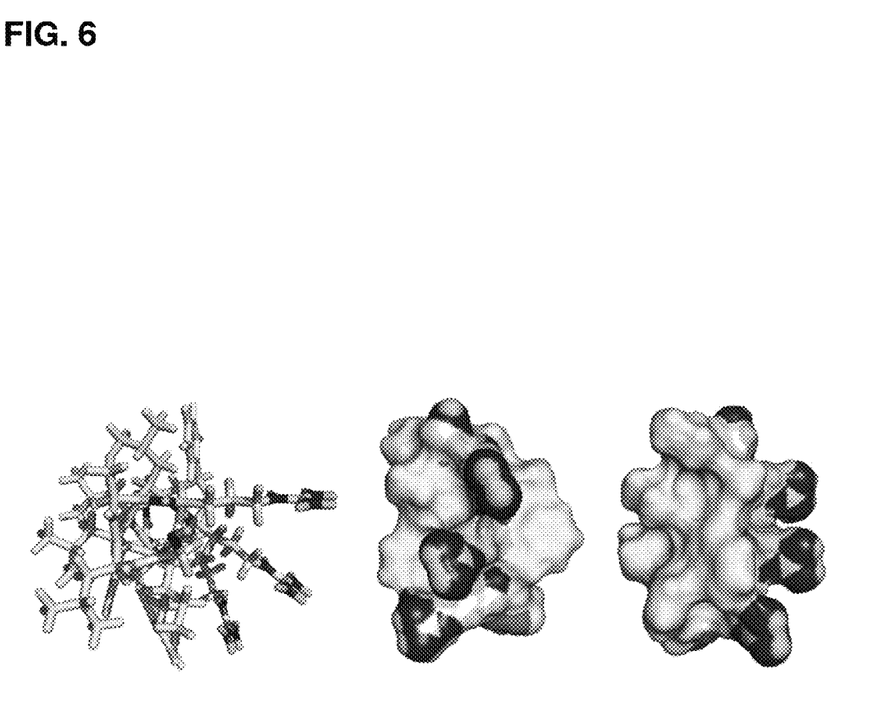
FIG. 6 depicts an antimicrobial agent (SEQ ID NO: 17) rendered as sticks (left; as shown above the helical axis) and solvent-accessible surface (center and right, as shown from front and side views, with the helical axis pointing up in the plane of the page). Coloration is as follows: hydrophobic residues are yellow; polar residues are colored by element (H=cyan, C=white, N=blue, O=red).

Among the four main mechanisms for cellular peptidic antimicrobial action, two (the barrel-stave and toroidal pore) models require stable amphiphilic helical peptides, and a third (in-plane diffusion) requires significant intramolecular stabilization as may be achieved by secondary (helices or sheets) or tertiary (disulphide bonds or salt bridges) structural elements that can guarantee preservation of peptidic amphiphilicity. For peptide families that are known to possess antimicrobial activity and have structural aspects indicative of helix formation (i.e., few or no prolines; sequence with polar-nonpolar alternating in period of about 4 monomers), it is reasonable to assume that the bioactive conformation of the peptide is helical, and that the mechanism of action is one of the three listed above. From this assumption, the antimicrobial agents provided herein have been tailored to have a high helical propensity (as predicted via the Agadir software) and to display substantial amphiphilicity in helical conformation. Such attributes are depicted in FIG. 5 for one of the most potent antimicrobial agents described herein, SEQ ID NO: 17.

Figure 7:
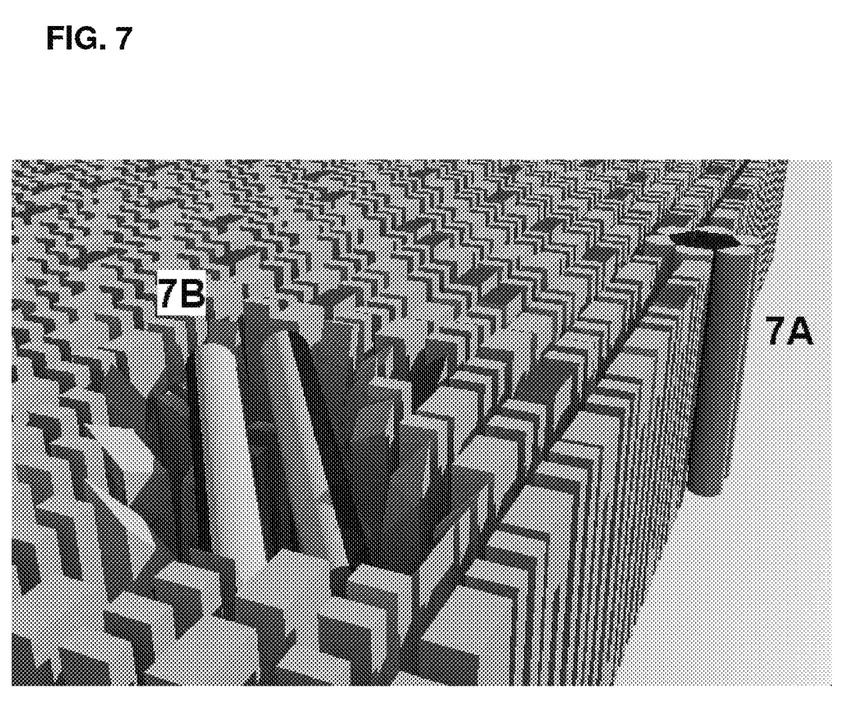
FIG. 7 shows a membrane disruption model. Toroidal pore formation (FIG. 7A) in which the peptide lipophilic surface coordinates the lipid medium in a systematic way, so as to collaboratively form a transmembrane pore, or in-plane diffusion (FIG. 7B). Individual peptides or dimers locally disrupt the membrane order via a combination of lipophilic peptide-membrane interactions and cationic attraction of the negatively charged phospholipid head groups (red surfaces) by positively charged peptide amino acids (blue surfaces), with the local pockets of disorder diffusively aggregating to form areas of significant membrane weakness.

The classic signature of the barrel-stave model is a periodic alternation of hydrophobic, anionic, hydrophobic and cationic patches, enabling the peptides to electrostatically self-assemble in cellular membranes into stable pores that exclude the surrounding lipids and compromise membrane integrity. The antimicrobial agents described herein are strictly cationic, thus obviating the barrel-stave model since a given peptide generally associates more preferentially with the lipid medium than with other peptides. However, they may still significantly interfere with the membrane via either of the remaining two possible models depicted in FIG. 7.

The high degrees of helical stability and amphiphilicity evident in the peptide formulations strongly suggests either the formation of toroidal pores which span microbe cell membranes inducing cell ion leakage (FIG. 7A), or else the formation of dimers whose selective lipid interactions disrupt the geometric regularity and stability of the lipid membrane, where these interaction include peptide cation interactions with lipid anions, and peptide aryl disruption of lipid aliphatic/aliphatic interactions.

Based on the examples described herein, the antimicrobially-potent peptide formulations based primarily on improving helical propensity and amphiphilicity profiles suggest that the observed activity arises from one of the above two mechanisms. The highly systematic nature of the peptides (rigorously hydrophobic, except for arginines in every fourth or fifth position) argues for the more structurally regular model of a toroidal pore (which could functionally assume the role of a voltage-gated channel to compromise cellular pH as per the KvAP peptide). However, the short length of antimicrobial agent peptides (~21 Å from end-to-end in helical conformation) implies that they may not be long enough to span the membrane, which would argue for the in-plane diffusion model.

Some very basic qualitative rules to explain observed antimicrobial activity trends have been resolved.
1) Given Trp in sequence position 4, peptide activity is proportional to the steric compactness of the lipophilic residue at position 3 (i.e., Pro>Ala>Val>Leu), which suggests that spatial compactness is optimal toward the N-terminus of the peptide,
2) If position 4 has anything other than a large lipophile, the backbone kink induced by proline is intolerable at position 3, and proline is not tolerated at all at any other position,
3) Given Arg in position 4, peptide activity varies according to Ala-3>Val-3>Leu-3>Pro-3, which is to say that spatial compactness is desirable, but the backbone kink induced by proline is unacceptable in this case, and
4) Interchanging residues at positions 12 and 13 does not have a major effect on activity, but significant changes to only one of these residues kills activity, indicating that the lipophilic/electropositive balance in this region is critical to activity.

To differentiate between the two mechanisms of action paradigms described in the previous section, one strategy would be to selectively substitute aromatic residues (i.e., Phe, Trp) for aliphatic (Ile, Leu) and vice versa. These substitutions should generally preserve the amphiphilicity that is required in both models, and some substitutions may enhance helical stability (which also favors both models), however their effect may vary as follows:
a) Aryl groups, being planar, are more compact than the branched alkyl groups in Ile and Leu side chains and stack better with the planar guanine groups in the requisite arginines, which may favor the formation of orderly pores that interface well with the membrane, while
b) Alkyl groups are inherently more attractive to the predominantly alkyl lipid medium, but their branched nature tends to produce more structural disorder as per the in-plane diffusion scenario.

Having elucidated some important structure/function trends, Agadir calculations on conservative substitutions (i.e., ones that change the size and electrostatic character of a residue a little but not much) were performed to further optimize the antimicrobial activity of the WB synthetic peptides. Therefore, the peptides listed below (SEQ ID NO: 26-33) were synthesized and evaluated to capitalize on their helical stability (Table 3).

TABLE 3

Antimicrobial agents optimized for helical stability.

| Peptide | | Sequence |
|---|---|---|
| WB14-F1 | (SEQ ID NO: 26) | GLARILLRLLFFRG |
| WB14-N1 | (SEQ ID NO: 27) | GLARILLRLLFRFG |
| WB14-O1 | (SEQ ID NO: 28) | GLVRILLRLLFRFG |
| WB14-O2 | (SEQ ID NO: 29) | GLVRILLRLLLRFG |
| WB14-O3 | (SEQ ID NO: 30) | SLVRILLRLLLRFG |
| WB14-O4 | (SEQ ID NO: 31) | GLTRILLRLLLRFG |
| WB14-O5 | (SEQ ID NO: 32) | GLVRILLRLLLRYG |
| WB14-O6 | (SEQ ID NO: 33) | GLVRILLRLLLRFS |

Example 3

Antimicrobial Activity of Antimicrobial Agent Analogs

The additional antimicrobial agent analogs optimized for helical stability in Example 2 (Table 3) were evaluated for antimicrobial activity. The antimicrobial activity of the synthetic analogues provided in Table 3 were evaluated using standard techniques such as those described in Sang, et al. 2007 Dev. Comp. Immunol., and herein incorporated by reference. The antimicrobial activity of the agents is provided in Table 4.

TABLE 4

Antimicrobial Activity of helical stability optimized agents against
*Staphylococcus aureus* (Minimum Inhibitory Concentration: MIC in µg/ml).

| Peptide | SEQ ID NO. | Sequence | MIC duplicates |
|---|---|---|---|
| WB14-A | SEQ ID NO: 3 | GLPWILLRWLFFRG | 8.0, 16.0 |
| WB14-F | SEQ ID NO: 8 | GLARILLRWLFFRG | 2.0, 4.0 |
| WB14-N | SEQ ID NO: 16 | GLARILLRWLFRFG | 4.0, 4.0 |
| WB14-O | SEQ ID NO: 17 | GLVRILLRWLFRFG | 16.0, 8.0 |
| WB14-F1 | SEQ ID NO: 26 | GLARILLRLLFFRG | 8.0, 8.0 |
| WB14-N1 | SEQ ID NO: 27 | GLARILLRLLFRFG | 128, 128 |
| WB14- | SEQ ID NO: 28 | GLVRILLRLLFRFG | 64, 128 |
| WB14- | SEQ ID NO: 29 | GLVRILLRLLLRFG | 256, 128 |
| WB14- | SEQ ID NO: 30 | SLVRILLRLLLRFG | 128, 128 |
| WB14- | SEQ ID NO: 31 | GLTRILLRLLLRFG | 256, 256 |
| WB14- | SEQ ID NO. 32 | GLVRILLRLLLRYG | 64, 128 |
| WB14- | SEQ ID NO. 33 | GLVRILLRLLLRFS | >256, >256 |

The results indicated that the antimicrobial agent having SEQ ID NO: 8 was the most efficacious antimicrobial synthetic peptide. The antimicrobial activity of SEQ ID NO. 8 was further evaluated against clinical isolates of mastitis-causing bacteria (Table 5).

TABLE 5

In vitro antimicrobial activity of the WB-14F peptide (SEQ ID NO.: 8) against clinical isolates of mastitis-causing bacteria.

| Clinical Isolate | Bacterial strain | Multidrug resistance | MIC (µg/ml) |
|---|---|---|---|
| 335-B05 | *Streptococcus dysgalactiae* | ++ | 8.0 |
| 335-B15 | *Klebsiella pneumoniae* | ++++ | 16.0 |
| 404-C18 | *Corynebacterium species* | ++ | 16.0 |
| 416-B10 | *Staphylococcus aureus* | +++ | 2.0 |
| 212-B05 | *Escherichia coli* | ++ | 4.0 |
| BAA 44* (ATCC) | *Staphylococcus aureus* | +++++ | 4.0 |

The WB-14F was synthesized under the following conditions: >95% purity; TFA salt; All were L-amino acids; No terminal modification; *ATCC cat. No. BAA 44.

Example 4

In Vivo Analysis of Antimicrobial Activity

The antimicrobial agent of SEQ ID NO: 8 was evaluated using an in vivo model of bacterial infection to assess the antimicrobial activity of the agent. The following methods and materials were used.

Bacterial strain. *Staphylococcus aureus* was isolated from milk from dairy cows with clinical mastitis (Livestock Disease Diagnostic Center, University of Kentucky. Lexington, Ky.). Upon arrival, bacteria were striped on blood agar plates (TSA+5% sheep blood from Remel, Kansas City. MO) and cultured at 37° C. for 24 hrs. A fresh single bacterial colony picked from the agar plate was inoculated into 10 ml of Muller Hinton II broth (MHB) and cultured at 37° C. for 4-6 hrs. until reaching an absorbance of 0.8 with a 625 nm spectrophotometer filter. At this absorbance, the MHB has been documented to contain $1\times10^5$ colony forming units (CFU) in a 50 µl volume.

Synthesis of the Water Buffalo Host Defense Peptide. The WB-14F peptide (SEQ ID NO: 8; GLARILLRWLFFRG) was chemically synthesized (Peptide2.0; Chantilly, Va.). After synthesis, the WB-14F molecule eluted in a single peak on RP-HPLC, and confirmed by mass spectroscopy. Final purity of the peptide was >97% with a molecular weight of 1718.4. The peptide was lyophilized and stored at −80° C. until use.

Mastitis mouse model. For the experiment, 56 female Balb/c mice (BW ~50 g) at 7-10 days of lactation were used. Four groups of n=14 mice were used for each experiment as described below. For intramammary inoculation the protocol described by Chandler was followed (*J. Med. Microbiol.* V3; 273-282: 1970) with minor modifications. Briefly, lactating mothers were separated from the pups 4 hours before inoculation. Then, pups were allowed to lactate for 1 hour before inoculation to empty the mammary glands. Pups were separated again from the mother and never reunited with her afterwards. After that, mice were anesthetized with a combination of Tiletamine/Zolazepam (Zoletil® 100, Virbac) at a dose of 100 mg/kg IM, and the mammary glands were disinfected with 70% alcohol. Using a stereoscopic microscope a 50 µL of the previously prepared *S. aureus* suspension (containing $1\times10^5$ CFU) was inoculated intra-mammarily. Injections were made slowly, using a 33 G needle (Hamilton, Kent, UK), into the left and right abdominal teats (L4 and R4). After inoculation mice were allowed to recover from the anesthesia.

Therapeutic effect of the WB-14F compared to controls and antibiotic treated groups. Mice (n=14/group) were treated intra-mammarily using the stereoscopic technique as follows: Group 1: WB-14F (32 µg diluted in 50 µl sterile PBS per gland); Group 2: Control, Sterile Phosphate Buffered Saline (50 µl per gland); Group 3: Ceptiofur (400 µg diluted in 50 µl mineral oil per gland); Group 4: infected but untreated. All groups (except Group 4) received the treatments 24 hours post-infection every 24 hrs. for 3 consecutive days (total of 3 treatments).

Determination of colony forming units (CFU) in mammary glands. All mice were euthanized (using $CO_2$) following the AVMA euthanasia guidelines 24 hours after the last treatment. The infected mammary glands (L4 and R4) were removed individually using soft tissue dissection and homogenized in 1 ml of sterile PBS in Falcon tubes using a Polytron tissue homogenizer (Kinematica, Switzerland). Dilutions ($10^{-1}$, $10^{-2}$, and $10^{-3}$) of the homogenates were plated quantitatively to determine the number of CFU per gland. Results were reported as the average of the results from the two glands (L4 and R4) from each animal.

Statistical Analysis. Kruskal-Wallis with Dunn's post-test was performed using GraphPad Prism Ver.5.0a for Mac, GraphPad Software, San Diego Calif. USA. A statistically significant difference (P<0.001) was found between the groups (FIG. 5), with the post-hoc test showing a difference between the WB-14F versus the three control groups (PBS, ATBX, and N1901.27on-Tx) at a 5% level of significance.

Example 5

Structural/Functional Analysis of Linked Dimer Peptide Antimicrobial Agents

A key component of the preliminary design and screening of covalently-linker peptide dimer formulations entailed the use of molecular dynamics simulations.

Figure 1:
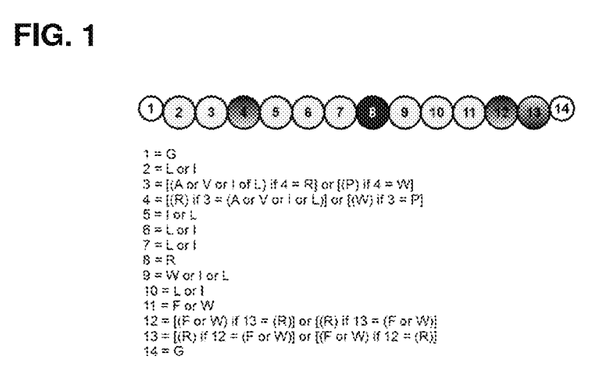
FIG. 1 graphically illustrates the amino acid composition of some antimicrobial agent aspects. Residue colors reflect a preference for lipophilic (yellow) or basic (blue).
Figure 2:
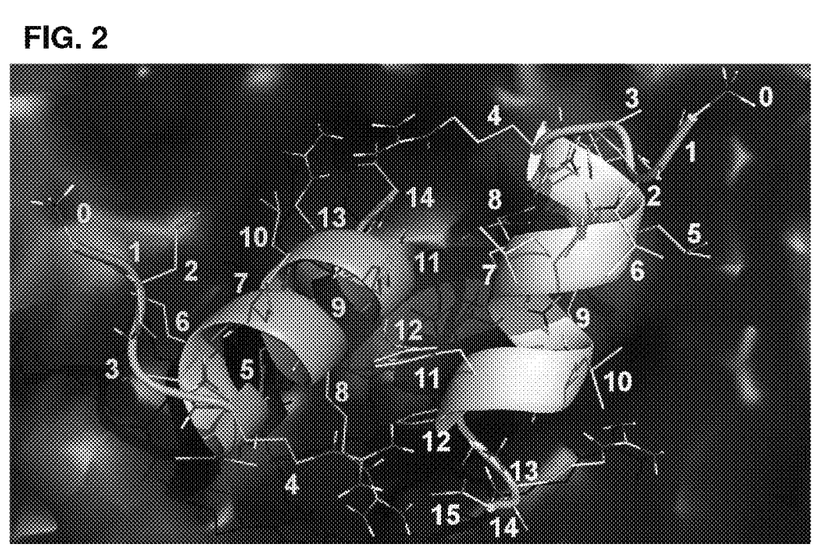
FIG. 2 shows the antimicrobially active dimer structure based on molecular dynamics simulations. Green and yellow objects are two compositionally identical peptides oriented in antiparallel alignment. Numbers identify the specific amino acid positions including the amino terminus (position 0) and the carboxy terminus (position 15). The solid surface represents the lipid membrane colored according to neutral (blue) or anionic (red) lipid.
Figure 3:
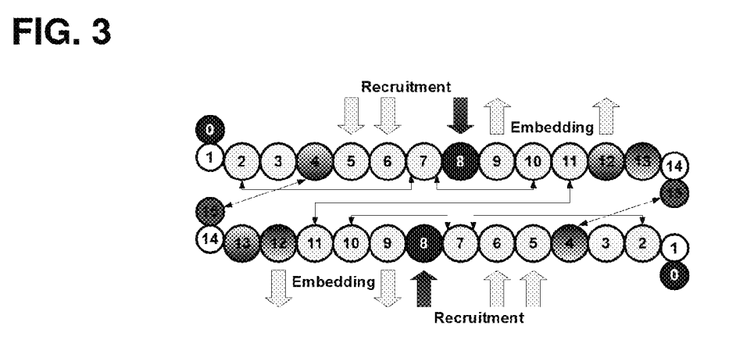
FIG. 3 graphically illustrates the roles for specific amino acid positions within the noncovalent dimer construct for some antimicrobial agent aspects. The illustration shows intradimer stabilizations (black arrows), dimer-membrane lipid interactions (yellow arrows) and dimer-membrane electrostatic coupling (red-blue arrows).
Figure 4:
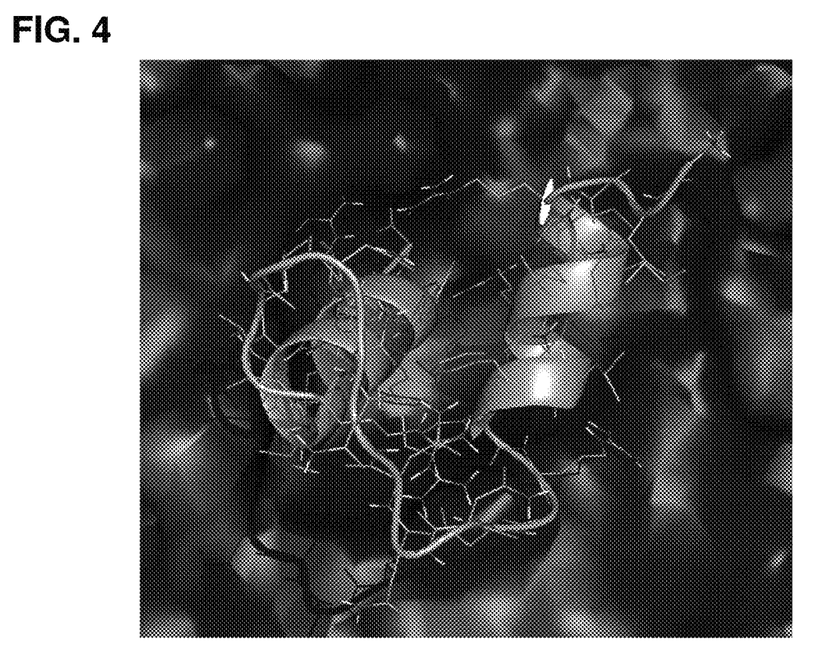
FIG. 4 graphically illustrates a minimally-spanned covalently-linked dimer based on the non-covalent formulation shown in FIG. 1. The dimer (silver cartoon and CPK-colored sticks) is shown on a model membrane surface, colored by neutral (blue) vs. anionic (red) lipids.

The sequence-specific activity dependence observed from in vivo studies is closely corroborated by intradimer interactions observed in molecular dynamics simulations of unlinked (non-covalent) peptide dimers. Subsequent molecular dynamics simulations have produced strong evidence that the interactions evident in the non-covalent dimers (shown graphically in FIG. 3) are preserved or amplified in specially-formulated covalently-linked dimers (as shown in FIG. 4).

Key structural features of the non-covalent and covalently-linked dimer systems that best corroborate experimental in vivo activities include 1) preservation of monomer helical structure, 2) retention of intradimer lipophilic and electrostatic coupling, plus strong evidence of both of the following intermolecular interactions: 3) peptide/membrane nonpolar coupling whereby peptide aryl amino acids interact with membrane lipids so as to insert aryl groups between individual lipid molecules, and 4) peptide/membrane electrostatic coupling between peptide cationic residues and anionic lipid head groups. For each of these four interaction classes, specific quantitative metrics were defined based on the relative percentage of simulation time in which specific atoms of the peptide reside within set distances of specific atoms of the intramolecular or intermolecular interaction partners. Specifically, consistent preservation of non-polar interatomic distances of no more than 4.0 Angstroms were used to identify preservation of key nonpolar features, and consistent preservation of polar interatomic distances of no more than 2.5 Angstroms were used to identify preservation of key polar features.

The four structural features described above were found via molecular dynamics simulations to be particularly well preserved or amplified by the following specific covalent linker formulations: DNNNNNN (SEQ ID NO: 34); DGGGGGG (SEQ ID NO: 38); DNNNNN (SEQ ID NO: 35); and, DGGGGG (SEQ ID NO: 37), where in each of the above cases the N-terminus of linker sequence covalently couples via a normal peptide bond to the C-terminus of the first peptide monomer, and the C-terminus of the linker sequence covalently couples via a normal peptide bond to the N-terminus of the second peptide monomer.

The invention illustratively disclosed herein suitably may be practiced in the absence of any element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the disclosure are deemed to be covered by the disclosure, which is limited only by the claims which follow.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09029319B1). An electronic copy of the "Sequence Listing" will also be available from the USPTO upon request and payment of the fee set forth in 37 CFR 1.19(b)(3).

What is claimed is:

1. An antibiotic peptide comprising:
   a. a first synthetic amino acid sequence having the sequence of formula 1
   Gly-$X_1$-$X_2$-$X_3$-$X_1$-$X_1$-$X_1$-Arg-$X_4$-$X_1$-$X_5$-$X_6$-$X_6$-Gly
   wherein
   $X_1$ is selected from the group of Leu or Ile,
   $X_2$ is selected from the group of Ala, Val, Leu, or Ile,
   $X_3$ is selected from the group of Arg or Trp,
   $X_4$ is selected from the group of Trp, Ile, or Leu
   $X_5$ is selected from the group of Phe or Trp, and
   $X_6$ is selected from the group of Phe, Trp, or Arg;
   b. a second synthetic amino acid sequence having the sequence of formula 1
   Gly-$X_1$-$X_2$-$X_3$-$X_1$-$X_1$-$X_1$-Arg-$X_4$-$X_1$-$X_5$-$X_6$-$X_6$-Gly
   wherein
   $X_1$ is selected from the group of Leu or Ile,
   $X_2$ is selected from the group of Ala, Val, Leu, or Ile,
   $X_3$ is selected from the group of Arg or Trp,
   $X_4$ is selected from the group of Trp, Ile, or Leu
   $X_5$ is selected from the group of Phe or Trp, and
   $X_6$ is selected from the group of Phe, Trp, or Arg; and,
   c. a linker sequence, wherein the linker sequence operably connects the first amino acid sequence and the second amino acid sequence.

2. The antimicrobial composition of claim 1, wherein the linker sequence forms a covalently linked peptide dimer of the first synthetic amino acid sequence and the second synthetic amino acid sequence.

3. The antimicrobial composition of claim 1, wherein the linker sequence is an amino acid sequence having the sequence of formula 2
A1-P2-P3- . . . Pn
wherein
A is an anionic amino acid residue,
P is a polar amino acid residue, and,
n is an integer selected from the group consisting of 3, 4, 5, 6, 7, 8, 9, 10, 11, 12, 13, 14, and 15.

4. The antimicrobial composition of claim 3, wherein the linker sequence is selected from the group consisting of SEQ ID NO: 34, SEQ ID NO: 35, SEQ ID NO: 36, SEQ ID NO: 37, SEQ ID NO: 38, and SEQ ID NO: 39.

5. The antimicrobial composition of claim 1, wherein the composition inhibits growth of bacteria.

6. The antimicrobial composition of claim 5, wherein the bacteria are selected from the group consisting of *Pseudomonas, Escherichia, Staphylococcus, Streptococcus, Enterococcus, Mycobacteria, Haemophilus*, and combinations thereof.

7. The antimicrobial composition of claim 1 further comprising a pharmaceutical carrier.

8. The antimicrobial composition of claim 1, wherein the first synthetic amino acid sequence and the second synthetic amino acid sequence are the same.

9. The antimicrobial composition of claim 1, wherein the second synthetic amino acid sequence is not the sequence of the first synthetic amino acid sequence.

10. The antimicrobial composition of claim 1, wherein the first synthetic amino acid sequence has at least 85% sequence identity to SEQ ID NO: 8.

11. The antimicrobial composition of claim 2, wherein the second synthetic amino acid sequence has at least 85% sequence identity to SEQ ID NO: 8.

12. A method for inhibiting growth of bacteria comprising contacting the bacteria, for a time and under conditions effective to inhibit bacteria growth, with a composition comprising
   a. a first synthetic amino acid sequence having the sequence of formula 1
      Gly-$X_1$-$X_2$-$X_3$-$X_1$-$X_1$-$X_1$-Arg-$X_4$-$X_1$-$X_5$-$X_6$-$X_6$-Gly
      wherein
      $X_1$ is selected from the group of Leu or Ile,
      $X_2$ is selected from the group of Ala, Val, Leu, or Ile,
      $X_3$ is selected from the group of Arg or Trp,
      $X_4$ is selected from the group of Trp, Ile, or Leu
      $X_5$ is selected from the group of Phe or Trp, and
      $X_6$ is selected from the group of Phe, Trp, or Arg;
   b. a second synthetic amino acid sequence having the sequence of formula 1
      Gly-$X_1$-$X_2$-$X_3$-$X_1$-$X_1$-$X_1$-Arg-$X_4$-$X_1$-$X_5$-$X_6$-$X_6$-Gly
      wherein
      $X_1$ is selected from the group of Leu or Ile,
      $X_2$ is selected from the group of Ala, Val, Leu, or Ile,
      $X_3$ is selected from the group of Arg or Trp,
      $X_4$ is selected from the group of Trp, Ile, or Leu
      $X_5$ is selected from the group of Phe or Trp, and
      $X_6$ is selected from the group of Phe, Trp, or Arg; and,
   c. a linker sequence, wherein the linker sequence operably connects the first amino acid sequence and the second amino acid sequence.

13. The method of claim 12, wherein the linker sequence forms a covalently linked peptide dimer of the first synthetic amino acid sequence and the second synthetic amino acid sequence.

14. The method of claim 12, wherein the linker sequence is an amino acid sequence having the sequence of formula 2
   A1-P2-P3-. . . Pn
   wherein
   A is an anionic amino acid residue,
   P is a polar amino acid residue, and,
   n is an integer selected from the group consisting of 3, 4, 5, 6, 7, 8, 9, 10, 11, 12, 13, 14, and 15.

15. The method of claim 14, wherein the linker sequence is selected from the group consisting of SEQ ID NO: 34, SEQ ID NO: 35, SEQ ID NO: 36, SEQ ID NO: 37, SEQ ID NO: 38, and SEQ ID NO: 39.

16. The method of claim 12, wherein the bacteria are selected from the group consisting of *Pseudomonas, Escherichia, Staphylococcus, Streptococcus, Enterococcus, Mycobacteria, Haemophilus,* and combinations thereof.

17. The method of claim 12, wherein the bacteria is selected from the group consisting of *Streptococcus agalactiae, Staphylococcus aureus, Enterobacter aerogenes, Klebsiella pneumoniae, Actinomyces pyogenes, Streptococcus uberis, Streptococcus dysgalactiae,* and combinations thereof.

18. The method of claim 12, wherein the growth of a microorganism is inhibited at least 10%.

19. A method of treating microbial infection, the method comprising:
   a. identifying a subject having a microbial infection; and,
   b. administering a therapeutically effective amount of an antibiotic composition to the subject, wherein the antibiotic composition comprises
      i. a first synthetic peptide having the sequence of formula 1:
         Gly-$X_1$-$X_2$-$X_3$-$X_1$-$X_1$-$X_1$-Arg-$X_4$-$X_1$-$X_5$-$X_6$-$X_6$-Gly
         wherein
         $X_1$ is selected from the group of Leu or Ile,
         $X_2$ is selected from the group of Ala, Val, Leu, or Ile,
         $X_3$ is selected from the group of Arg or Trp,
         $X_4$ is selected from the group of Trp, Ile, or Leu
         $X_5$ is selected from the group of Phe or Trp, and
         $X_6$ is selected from the group of Phe, Trp, or Arg;
      ii. a second synthetic amino acid sequence having the sequence of formula 1:
         Gly-$X_1$-$X_2$-$X_3$-$X_1$-$X_1$-$X_1$-Arg-$X_4$-$X_1$-$X_5$-$X_6$-$X_6$-Gly
         wherein
         $X_1$ is selected from the group of Leu or Ile,
         $X_2$ is selected from the group of Ala, Val, Leu, or Ile,
         $X_3$ is selected from the group of Arg or Trp,
         $X_4$ is selected from the group of Trp, Ile, or Leu
         $X_5$ is selected from the group of Phe or Trp, and
         $X_6$ is selected from the group of Phe, Trp, or Arg; and,
      iii. a linker sequence, wherein the linker sequence operably connects the first amino acid sequence and the second amino acid sequence.

20. The method of claim 19, wherein the antibiotic composition further comprises a pharmaceutical carrier.

21. The method of claim 19 further comprising inhibiting the growth of a mastitis infection causing microorganism by at least 10%.

22. The method of claim 19, wherein the linker sequence forms a covalently linked peptide dimer of the first synthetic amino acid sequence and the second synthetic amino acid sequence.

23. The method of claim 19, wherein the linker sequence is an amino acid sequence having the sequence of formula 2
   A1-P2-P3-. . . Pn
   wherein
   A is an anionic amino acid residue,
   P is a polar amino acid residue, and,
   n is an integer selected from the group consisting of 3, 4, 5, 6, 7, 8, 9, 10, 11, 12, 13, 14, and 15.

24. The method of claim 23, wherein the linker sequence is selected from the group consisting of SEQ ID NO: 34, SEQ ID NO: 35, SEQ ID NO: 36, SEQ ID NO: 37, SEQ ID NO: 38, and SEQ ID NO: 39.

25. A method of treating mastitis, the method comprising:
   a. identifying a subject having mastitis; and,
   a. administering a therapeutically effective amount of an antibiotic composition to the subject, wherein the antibiotic composition comprises
      i. a first synthetic peptide having the sequence of formula 1:
         Gly-$X_1$-$X_2$-$X_3$-$X_1$-$X_1$-$X_1$-Arg-$X_4$-$X_1$-$X_5$-$X_6$-$X_6$-Gly
         wherein
         $X_1$ is selected from the group of Leu or Ile,
         $X_2$ is selected from the group of Ala, Val, Leu, or Ile,
         $X_3$ is selected from the group of Arg or Trp,
         $X_4$ is selected from the group of Trp, Ile, or Leu
         $X_5$ is selected from the group of Phe or Trp, and
         $X_6$ is selected from the group of Phe, Trp, or Arg;
      ii. a second synthetic amino acid sequence having the sequence of formula 1:
         Gly-$X_1$-$X_2$-$X_3$-$X_1$-$X_1$-$X_1$-Arg-$X_4$-$X_1$-$X_5$-$X_6$-$X_6$-Gly
         wherein
         $X_1$ is selected from the group of Leu or Ile,
         $X_2$ is selected from the group of Ala, Val, Leu, or Ile,
         $X_3$ is selected from the group of Arg or Trp,
         $X_4$ is selected from the group of Trp, Ile, or Leu $X_5$ is selected from the group of Phe or Trp, and
$X_6$ is selected from the group of Phe, Trp, or Arg; and,
iii. a linker sequence, wherein the linker sequence operably connects the first amino acid sequence and the second amino acid sequence.

26. The method of claim 25, wherein the antibiotic composition is administered to the mammary tissue of the subject.

27. The method of claim 25 further comprising inhibiting the growth of a mastitis infection causing microorganism by at least 10%.

28. The method of claim 25, wherein the linker sequence forms a covalently linked peptide dimer of the first synthetic amino acid sequence and the second synthetic amino acid sequence.

* * * * *